(12) United States Patent
Charette et al.

(10) Patent No.: US 7,507,709 B2
(45) Date of Patent: *Mar. 24, 2009

(54) SYNERGISTIC EFFECTS OF OP/BMP MORPHOGENS AND GDNF/NGF NEUROTROPHIC FACTORS

(75) Inventors: Marc F. Charette, Needham, MA (US); Ted Ebendal, Uppsala (SE); David C. Rueger, Southborough, MA (US)

(73) Assignee: Stryker Corporation, Kalamazoo, MI (US)

( * ) Notice: Subject to any disclaimer, the term of this patent is extended or adjusted under 35 U.S.C. 154(b) by 249 days.

This patent is subject to a terminal disclaimer.

(21) Appl. No.: 11/083,512

(22) Filed: Mar. 18, 2005

(65) Prior Publication Data
US 2005/0164938 A1   Jul. 28, 2005

Related U.S. Application Data

(63) Continuation of application No. 09/508,254, filed as application No. PCT/US98/18772 on Sep. 9, 1998, now Pat. No. 6,936,582.

(60) Provisional application No. 60/058,258, filed on Sep. 9, 1997.

(51) Int. Cl.
*A61K 38/18* (2006.01)
*C07K 14/48* (2006.01)
*C07K 14/51* (2006.01)

(52) U.S. Cl. .......................... 514/2; 530/399
(58) Field of Classification Search ............ None
See application file for complete search history.

(56) References Cited

U.S. PATENT DOCUMENTS

| 5,851,832 | A   | 12/1998 | Weiss et al. |
| 6,294,346 | B1  | 9/2001  | Weiss et al. |
| 6,949,505 | B1* | 9/2005  | Rueger et al. .......... 514/2 |

FOREIGN PATENT DOCUMENTS

| WO | WO 92/00392 | 1/1992 |
| WO | WO 96/18735 | 6/1996 |
| WO | WO 97/21447 | 6/1997 |

OTHER PUBLICATIONS

Mehler et al. Bone morphogenetic proteins in the nervous system. Trends in Neurosciences. vol. 20, pp. 309-317 (Jul. 1997).*

Jordan et al. Bone morphogenetic proteins:neurotrophic roles for midbrain dopaminergic neurons and implications of astroglial cells. Abstract European Journal of Neuroscience. vol. 9/8, pp. 1699-1709 (Aug. 1997).*

On-line Medical Dictionary. Published at the Centre for Cancer Education, University of Newcastle upon Tyne. The CancerWEB Project. http://cancerweb.ncl.ac.uk/cgi-bin/omd?query=central+nervous+system (Copyright 1997-2005).*

Jordan et al., Bone Morphogenetic Proteins:Neurotrophic roles for midbrain dopaminergic neurons and implications for astroglial cells. European Journal of Neuroscience, vol. 9/8, pp. 1699-1709 (Aug. 1997).*

Jones et al., 1991, "Involvement of Bone Morphogenetic Protein-4 (BMP-4) and Vgr-1 in morphogenesis and neurogenesis in the mouse," Development 111:531-542.

Bengtsson et al., 1998, Potentiating Interactions Between Morphogenetic Protein and Neurotrophic Factors in Developing Neurons. J. Neuroscience Res. 53:559-568.

Buckel, 1996, Recombinant proteins for therapy. TiPS 17:450-456.

Durbec et al., 1996, GDNF signalling through the Ret receptor tyrosine kinase, Nature 381:789-793.

Freshney, 1983, Culture of Animal Cells. A Manual of Basic Technique. Alan R. Liss, Inc. New York.

Jackowski, 1995, Neural injury repair: hope for the future as barriers to effective CNS regeneration become clearer. British J. Neurosurgery 9:303-317.

Lein et al., 1996, The Effects of Extracellular Matrix and Osteogenic Protein-1 on the Morphological Differentiation of Rat Sympathetic Neurons, J. Dev. Neuro. 14(3):203-215.

Ngo et al., 1994, Computational Complexity, Protein Structure Prediction and the Levinthal Paradox. the Protein Folding Problem and Tertiary Structure Prediction. Birkhauser Boston, pp. 492-485.

Trupp et al., 1995, Peripheral Expression and Biological Activities of GDNF, a New Neurotrophic Factor for Avian and Mammalian Peripheral Neurons. J. Cell Biol. 130(1):137-148.

(Continued)

*Primary Examiner*—Marianne P Allen
*Assistant Examiner*—Regina M DeBerry
(74) *Attorney, Agent, or Firm*—Ropes & Gray LLP; James F. Haley, Jr.; Karen Mangasarian

(57) ABSTRACT

OP/BMP morphogen may be combined with GDNF/NGF neurotrophic factors to promote the survival or growth, or inhibit the death or degeneration, of mammalian cells, particularly neural cells, which express OP/BMP-activated serine/threonine kinase receptors and GDNF/NGF-activated tyrosine kinase receptors. Also disclosed are methods for the treatment of such cells, including treatments for mammals afflicted with, or at imminent risk of, damage or injury to, such cells, as well as new pharmaceutical preparations for such treatments.

10 Claims, 1 Drawing Sheet

OTHER PUBLICATIONS

Wells, 1990, Additivity of Mutational Effects in Proteins. Biochemistry 29:8509-8517.

Batchelor, P.E. et al. Nerve Growth Factor Receptor and Choline Acetyltransferase Colocalization in Neurons within the Rat Forebrain: Response to Fimbria-Fornix Transection. *J. Comp. Neurol.* 284, 187-204 (1989).

Beck et al. The Nature of the Trophic Action of Brain-Derived Neurotrophic Factor, des(1-3)-Insulin-Like Growth Factor-1, and Basic Fibroblast Growth Factor on Mesencephalic Dopaminergic Neurons Developing in Culture. *Neurosci.* 52, 855-866 (1993).

Bengtsson, H. et al. Potentiating Interactions Between Morphogenetic Protein and Neurotrophic Factors in Developing Neurons. *J. Neurosci. Res.* 53, 559-568 (1998).

Berkemeier et al. Neurotrophin-5: A Novel Neurotrophic Factor that Activates trk and trkB. *Neuron* 7, 857-866 (1991).

Bruckenstein, D.A. & Higgins, D. Morphological Differentiation of Embryonic Rat Sympathetic Neurons in Tissue Culture. *Dev. Biol.* 128, 324-336 (1988).

De Koninck, P. et al. NGF Induces Neonatal Rat Sensory Neurons to Extend Dendrites in Culture after Removal of Satellite Cells. *J. Neurosci.* 13, 577-585 (1993).

Durbec, P. et al. GDNF signaling through the Ret receptor tyrosine kinase. *Nature* 381, 789-793 (Jun. 27, 1996).

Ebendal, T. Function and Evolution in the NGF Family and its Receptors. *J. Neurosci. Res.* 32, 461-470 (1992).

Ernfors, P. et al. Molecular cloning and neurotrophic activities of a protein with structural similarities to nerve growth factor: Developmental and topographical expression in the brain. *PNAS* 87, 5454-5458 (Jul. 1990).

Hallbook, F. et al. Neurotrophins and their receptors in chicken neuronal development. *Int. J. Dev. Biol.* 39, 855-868 (1995).

Hefti, F. Neurotrophic Factor Therapy for Nervous System Degenerative Diseases. *J. Neurobiol.* 25, 1418-1435 (1994).

Hoffer et al. Glial cell line-derived neurotrophic factor reverses toxin-induced injury to midbrain dopaminergic neurons in vivo. *Neurosci. Letters* 182, 107-111 (1994).

Hudson, J. et al. Glial Cell Line-derived Neurotrophic Factor Augments Midbrain Dopaminergic Circuits in Vivo. *Brain Res. Bull.* 36, 425-432 (1995).

Hyman et al. BDNF is a neurotrophic factor for dopaminergic neurons of the substantia nigra. *Nature* 350, 230-232 (1991).

Ibanez, C. F. et al. Neurotrophin-4 is a target-derived neurotrophic factor for neurons of the trigeminal ganglion. *Development* 117, 1345-1353 (1993).

Ip, N.Y. et al. Mammalian neurotrophin-4: Structure, chromosomal localization, tissue distribution, and receptor specificity. *PNAS* 89, 3060-3064 (Apr. 1992).

Knusel, B. et al. Promotion of central cholinergic and dopaminergic neuron differentiation by brain-derived neurotrophic factor but not neurotrophin 3. *PNAS* 88, 961-965 (Feb. 1991).

Lein, P. et al. The Effects of Extracellular Matrix and Osteogenic Protein-1 on the Morphological Differentiation of Rat Sympathetic Neurons. *Int. J. Dev. Neurosci.* 14, 203-215 (1996).

Lein, P. et al. Osteogenic Protein-1 Induces Dendritic Growth in Rat Sympathetic Neurons. *Neuron* 15, 597-605 (Sep. 1995).

Lin, L.-F. H. et al. GDNF: A Glial Cell Line-Derived Neurotrophic Factor for Midbrain Dopaminergic Neurons. *Science* 260, 1130-1132 (1993).

Liu, F. et al. Human Type II REceptor for Bone Morphogenic Proteins (BMPs): Extension of the Two-Kinase Receptor Model to the BMPs. *Mol. Cell. Biol.* 15, 3479-3486 (Jul. 1995).

Lomko, I. Neurotrophins—An Update. *DN&P* 6, 669-671 (Nov. 1993).

Nosrat et al. Cellular expression of GDNF mRNA suggests multiple functions inside and outside the nervous system. *Cell Tiss. Res.* 286, 191-207 (1996).

Olson, L. Neurotrophins in Neurodegenerative Disease: Theoretical Issues and Clinical Trials. *Neurochem. J.* 25, 1-3 (1994).

Oppenheim et al. Developing motor neurons rescued from programmed and axotomy-induced cell death by GDNF. *Nature* 373, 344-346 (1995).

Pachnis, V. et al. Expression of the c-ret proto-oncogene during mouse embryogenesis. *Development* 119, 1005-1017 (1995).

Pei & Enbendal. Specific Lesions in the Extrapyramidal System of the Rat Brain Induced by 3-Nitropropionic Acid (3-NPA), *Exp. Neurol.* 132, 105-115 (1995).

Rosenzweig, B.L. et al. Cloning and characterization of a human type II receptor for bone morphogenic proteins. *PNAS* 92, 7632-7636 (Aug. 1995).

Sauer et al. Brain-derived neurotrophic factor enhances function rather than survival of intratriatal dopamine cell-rich grafts. *Brain Res.* 626, 37-44 (1993).

Schuchardt, A. et al. Defects in the kidney and enteric nervous system of mice lacking the tyrosine kinase receptory Ret. *Nature* 367, 380-383 (1994).

Snider, W.D. & Johnson, E.M. Neurotrophic Molecules. *Ann. Neurol.* 26, 489-506 (1989).

Snider, W.D. Nerve Growth Factor Enhances Dendritic Arborization of Sympathetic Ganglion Cells in Developing Mammals. *J. Neurosci.* 8, 2628-2634 (1988).

Soderstrom, S. et al. Expression of serine/threonine kinase receptors including the bone morphogenetic factor type II receptor in the developing and adult rat brain. *Cell Tiss. Res.* 286, 269-279 (1996).

Soderstrom, S. et al. The effect of mercury vapour on cholinergic neurons in the fetal brain: studies on the expression of nerve growth factor and its low- andn high-affinity receptors. *Dev. Brain Res.* 85, 96-108 (1995).

Tropea, M. et al. Glial Cells Promote Dendritic Development in Rat Sympathetic Neurons in Vitro. *Glia* 1, 380-392 (1988).

Trupp, M. et al. Functional receptor for GDNF encoded by the c-ret proto-oncogene. *Nature* 381, 785-789 (1996).

Vasquez, M.E. & Ebendal, T. Messenger RNAs for trk and the low-affinity NGF receptor in rat basal forebrain. *Neuro Report* 2, 593-596 (1991).

Williams, R. & Ebendal, T. Neurotrophin receptor expression during development of the chick spinal sensory ganglion. *Neuro Report* 6, 2277-2282 (1995).

Williams, R. et al. Developmentally Regulated Expressoin of mRNA for Neurotrophin High-Affinity (trk) Receptors within Chick Trigeminal Sensory Neurons. *Eur. J. Neurosci.* 7, 116-128 (1995).

Yan et al. In vivo neurotrophic effects of GDNF on neonatal and adult facial motor neurons. *Nature* 373, 341-344 (1995).

* cited by examiner

SYNERGISTIC EFFECTS OF OP/BMP MORPHOGENS AND GDNF/NGF NEUROTROPHIC FACTORS This application is a continuation of U.S. application Ser. No. 09/508,254, filed Oct. 2, 2000 now U.S. Pat. No. 6,936,582, which is a national stage filing under 35 U.S.C. § 371 of International Application No. PCT/US98/18772, filed Sep. 9, 1998, which claims the benefit of U.S. Provisional Application No. 60/058,258, filed Sep. 9, 1997.

FIELD OF THE INVENTION

The present invention relates generally to methods and preparations for the treatment of mammalian subjects afflicted with, or at imminent risk of, damage or injury to tissues, particularly neural tissues, which express receptors for OP/BMP morphogens and GDNF/NGF neurotrophic factors.

BACKGROUND OF THE INVENTION

During development of the mammalian nervous system, differentiating neurons from the central and peripheral nervous systems send out axons that must grow and make contact with specific target cells. In some cases, neurons stay confined entirely within the central nervous system. In other cases, however, growing axons must cover enormous distances, extending from the CNS into the periphery of the body. In mammals, this stage of neurogenesis is completed during the embryonic phase of life and, it is believed, neuronal cells do not multiply once they have fully differentiated.

Dendritic growth occurs in two phases: initial extension followed by elongation and ramification. Purves et al., *Nature* 336:123-128 (1988). Some molecules, including neurotransmitters and hormones, have been shown to regulate expansion of an existing dendritic arbor. Much less is known, however, about the factors that influence early events, and cause a neuron to initially form dendrites. In certain classes of neurons, initial dendritic sprouting occurs as part of an intrinsic developmental program which is relatively independent of trophic interactions. Dotti et al., *J. Neurosci.* 8:1454-1468 (1988). In other classes of neurons, however, the regulation of the initial stages of dendritic growth appears to be quite different. For example, rat sympathetic neurons fail to form dendrites and extend only axons when they are cultured in the absence of non-neuronal cells. In contrast, co-culture with Schwann cells or astrocytes causes these neurons to form dendritic processes and to eventually generate a dendritic arbor which is comparable in size to that observed in situ. Tropea et al, *Glia* 1:380-392 (1988). Thus, it would appear that specific trophic interactions are required to allow sympathetic neurons to form dendrites.

The foregoing observations have been taken to support a theory that the in situ environment specifies formation of a dendritic arbor. The environment in the vicinity of neural cells or developing neural processes is thought to include electromagnetic, electrochemical and/or biochemical fields or gradients which positively and negatively influence the extent and specificity of dendritic outgrowth as well as the formation of synapses between dendrites and nerve cell bodies and axons. This theory, however, suffers from a paucity of identified mediators which have the capacity to cause neurons to sprout dendrites.

A host of neuropathies, some of which affect only a subpopulation or a system of neurons in the peripheral or central nervous systems have been identified. The neuropathies, which may affect the neurons themselves or the associated glial cells, may result from cellular metabolic dysfunction, infection, exposure to toxic agents, autoimmunity dysfunction, malnutrition or ischemia. In some cases the cellular dysfunction is thought to induce cell death directly by apoptosis. Oppenheim, *Ann Rev. Neurosci.* 14:37-43 (1991). In other cases, the neuropathy may induce tissue necrosis by stimulating the body's immune system, resulting in a local inflammatory response and cell lysis at the initial site of neural injury.

The ability of neurons within the peripheral nervous system to regenerate a damaged neural pathway is limited. Specifically, new axons and dendrites extend randomly, and are often misdirected, making contact with inappropriate targets that can cause abnormal function. In addition, where severed nerve processes result in a gap of longer than a few millimeters, e.g., greater than 10 millimeters (mm), appropriate nerve regeneration does not occur, either because the processes fail to grow the necessary distance, or because of misdirected axonal growth. Efforts to repair peripheral nerve damage by surgical means has met with mixed results, particularly where damage extends over a significant distance. In some cases, the suturing steps used to obtain proper alignment of severed nerve ends stimulates the formulation of scar tissue which is thought to inhibit axon regeneration. Even where scar tissue formation has been reduced, as with the use of nerve guidance channels or other tubular prostheses, successful regeneration generally is still limited to nerve damage of less than 10 millimeters in distance.

It is now well established that various trophic factors play a critical role in regulating the survival and differentiation of developing neurons. Snider et al., *Ann. Neurol.* 26:489-506 (1989). Most of the characterized actions of nerve trophic actors relate to developmental events and suggest that the temporal and local regulation of expression of these proteins plays a role during maturation of the nervous system. Nerve trophic factors are also important in the function of the adult nervous system for the maintenance of structural integrity and regulation of plasticity. Such processes are altered in neurodegenerative diseases and neurodegenerative events following acute injury to the nervous system. This has prompted speculation that nerve trophic factors are involved in the structural alterations which occur in response to injury and disease.

Several well-characterized trophic factors have been shown to enhance the survival and differentiation of dopaminergic neurons in tissue culture and/or following transplantation to the anterior chamber of the eye. These trophic factors include fibroblast growth factor (FGF), epidermal growth factor (EGF), platelet-derived growth factor (PDGF), transforming growth factor-α (TGF-α), and glial cell-derived neurotrophic factor (GDNF), as well as several Nerve Growth Factor (NGF) Related Neurotrophins.

Nerve trophic factors are found among several protein superfamilies of polypeptide growth factors based on their amino acid sequence homology and/or their three-dimensional structure. MacDonald et al, *Cell* 73:421-424 (1993). One family of neurotrophic factors is the neurotrophin family. This family currently consists of Nerve Growth Factor (NGF), Brain Derived Neurotrophic Factor (BDNF), Neurotrophin-3 (NT-3), Neurotrophin-4/5 (NT-4/5), and Neurotrophin-6 (NT-6). These neurotrophic factors affect specific neuronal populations in the central nervous system. The loss of such specific neurotrophic factors may be responsible for age-related declines in cell survival and/or function. While the cellular source remains unclear, there is evidence to suggest that neurons and glial cells are both capable of secreting neurotrophic factors.

The osteogenic protein/bone morphogenetic protein (OP/BMP) proteins form a family, or subfamily, within the larger TGF-β superfamily of proteins. That is, these proteins form a distinct subgroup, referred to herein as the "OP/BMP family of morphogens" or "OP/BMP morphogens," within the loose evolutionary grouping of sequence-related proteins known as the TGF-β superfamily. Members of this protein family comprise secreted polypeptides that share common structural features, and that are similarly processed from a pro-protein to yield a carboxy-terminal mature protein. OP/BMP morphogens have been identified in developing and adult rat brain and spinal cord tissue, as determined both by northern blot hybridization of morphogen-specific probes to mRNA extracts from developing and adult nerve tissue and by immunolocalization studies. For example, northern blot analysis of developing rat tissue has identified significant OP-1 mRNA transcript expression in the CNS. The mRNA of another OP/BMP family member, GDF-1, appears to be expressed primarily in developing and adult nerve tissue, specifically in the brain, including the cerebellum and brain stem, spinal cord and peripheral nerves. BMP4 (also referred to as BMP2B) and Vgr-1 transcripts also have been reported to be expressed in nerve tissue.

The morphogen OP-1 was found to be localized predominantly to the extracellular matrix of the grey matter (neuronal cell bodies), distinctly present in all areas except the cell bodies themselves. In white matter, formed mainly of myelinated nerve fibers, staining appears to be confined to astrocytes (glial cells). A similar staining pattern also was seen in newborn rat (10 day old) brain sections.

In addition, OP-1 has been specifically localized in the substantia nigra, which is composed primarily of striatal basal ganglia, a system of accessory motor neurons whose function is associated with the cerebral cortex and corticospinal system. Dysfunctions in this subpopulation or system of neurons are associated with a number of neuropathies, including Huntington's chorea and Parkinson's disease.

SUMMARY OF THE INVENTION

The present invention is based, in part, upon the discovery that OP/BMP morphogens in combination with GDNF/NGF neurotrophic factors show a synergistic effect in promoting the survival or growth, or inhibiting the death or degeneration, of mammalian cells, particularly neural cells, which express OP/BMP-activated serine/threonine kinase receptors and GDNF/NGF-activated tyrosine kinase receptors. Based on this discovery, the present invention provides new methods for in vivo and in vitro treatment of such cells, including in vivo treatments for mammals afflicted with, or at imminent risk of, damage or injury to such cells, as well as new pharmaceutical preparations for such in vivo and in vitro treatments.

Thus, in one aspect, the present invention provides methods for promoting the survival or growth of mammalian cells, particularly neural cells, by contacting the cells with an effective concentration of a preparation comprising a GDNF/NGF neurotrophic factor and an OP/BMP morphogen. Similarly, the present invention provides methods for inhibiting the death or degeneration of mammalian cells, particularly neural cells, by contacting the cells with an effective concentration of a preparation comprising a GDNF/NGF neurotrophic factor and an OP/BMP morphogen. Such methods may be employed in vitro (e.g., for improved cell cultures) or in vivo (e.g., for treating conditions affecting such cells in a mammalian subject).

In another aspect, the present invention specifically provides methods for treating a mammalian subject afflicted with, or at imminent risk of, damage or injury to cells, particularly neural cells, comprising contacting the neural cells with an effective concentration of a preparation comprising a GDNF/NGF neurotrophic factor and an OP/BMP morphogen. These methods can be applied to either neurons or neuroglial cells, and to either central or peripheral nervous system cells.

The methods of the present invention are particularly suited to the treatment of cells which have been damaged or injured, or are at imminent risk of damage or injury, due to mechanical traumas such as blunt force traumatic brain injury, blunt force traumatic spinal cord injury, concussion, intracranial pressure due to cerebral edema or subdural haematoma, broken or crushed vertebra, and torn or severed nerves; chemical traumas such as those arising from exposure to neurotoxins or the side effects of chemotherapies; ischemic injuries such as those arising from stroke, cardiac arrest or failure; and neuropathic or neurodegenerative damage or injury such as those arising from neuropathic diseases including Parkinson's disease, Huntington's disease, Amyotrophic Lateral Sclerosis, Alzheimer's disease, epilepsy, progressive muscular atrophy, Charcot-Marie-Tooth disease, palsy, dementia, Shy-Drager disease, Wernicke-Korsakoff syndrome, and Hallervorden-Spatz disease.

In preferred embodiments, the OP/BMP morphogens of the present invention comprise polypeptides having amino acid sequences with at least 70% homology, more preferably 80% homology, with the C-terminal seven-cysteine domain of human OP-1. In particularly preferred embodiments, the OP/BMP morphogens comprise polypeptides having at least 60% amino acid identity, more preferably at least 70% identity, with the C-terminal seven-cysteine domain of human OP-1. In most preferred embodiments, the OP/BMP morphogen comprises at least the C-terminal six- or seven-cysteine domain of a mammalian, preferably human, OP-1, OP-2, OP-3, BMP2, BMP3, BMP4, BMP5, BMP6, or BMP9 protein. Preferably, the OP/BMP morphogens of the present invention are capable of inducing osteogenesis in the Reddi-Sampath ectopic bone assay.

In preferred embodiments, the GDNF/NGF neurotrophic factors of the present invention comprise at least the mature, functional form of a mammalian, preferably human, GDNF, NGF, BDNF, NT-3, NT-4, NT-5 or NT-6 protein.

In preferred embodiments the effective concentration of the preparation comprises between 0.1 ng/ml and 10 µg/ml of an OP/BMP morphogen and between 0.1 ng/ml and 10 µg/ml of a GDNF/NGF neurotrophic factor, more preferably between 1 ng/ml and 100 ng/ml of either an OP/BMP morphogen or a GDNF/NGF neurotrophic factor and, most preferably, between 1 ng/ml and 100 ng/ml of both an OP/BMP morphogen and a GDNF/NGF neurotrophic factor.

In another aspect, the present invention provides methods for promoting the survival or growth, or inhibiting the death or degeneration, of mammalian cells, including non-neural cells, which express an OP/BMP-activated serine/threonine kinase receptor and a GDNF/NGF-activated tyrosine kinase receptor. Similarly, the present invention provides methods for treating a mammalian subject afflicted with damage or injury to cells, or at imminent risk of damage or injury to cells, including non-neural cells, which express an OP/BMP-activated serine/threonine kinase receptor and a GDNF/NGF-activated tyrosine kinase receptor. These methods also comprise contacting such cells with an effective concentration of a preparation comprising a GDNF/NGF neurotrophic factor and an OP/BMP morphogen, as described above.

In another aspect, the present invention provides for pharmaceutical preparations for promoting the survival or growth of mammalian cells, or inhibiting the death or degeneration of mammalian cells, particularly neural cells, comprising a GDNF/NGF neurotrophic factor in combination with an OP/BMP morphogen.

The preferred methods, materials, and examples that will now be described are illustrative only and are not intended to be limiting. Other features and advantages of the invention will be apparent from the following detailed description, and from the claims.

DETAILED DESCRIPTION OF THE INVENTION

Figure 1A:
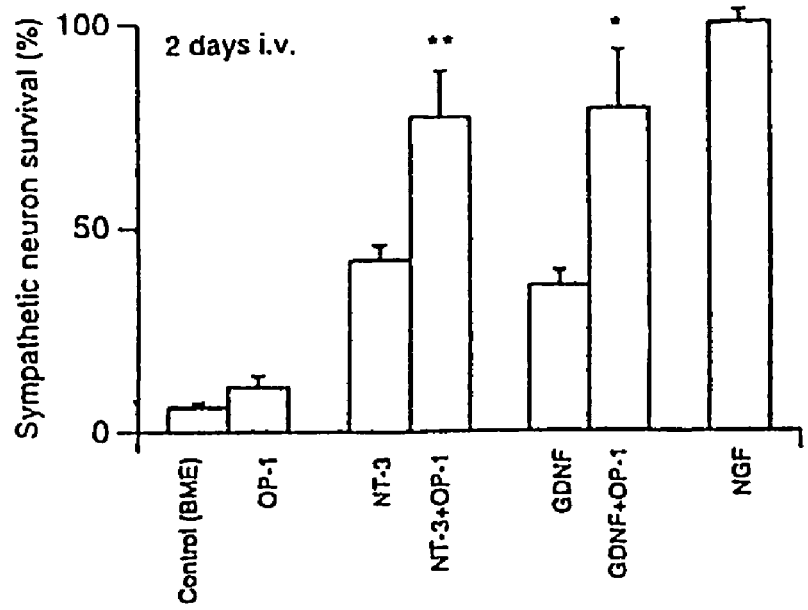
FIGS. 1A and 1B are bar graphs showing the survival of dissociated sympathetic neurons grown in collagen gels after 2 or 6 day treatments, respectively, with NT-3 (2 ng/ml) or GDNF (50 ng/ml), in the presence or absence of OP-1.

The present invention provides new methods of treatment for mammalian subjects afflicted with, or at imminent risk of, damage or injury to tissues, particularly neural tissues, comprising the administration of a combination of an OP/BMP morphogen and a GDNF/NGF neurotrophic factor. Surprisingly, it has been demonstrated that administration of these agents in combination has a synergistic effect in promoting the survival and/or growth of neural tissues, and in inhibiting death or degeneration of neural tissues. In addition, the present invention provides new pharmaceutical preparations comprising an OP/BMP morphogen in combination with a GDNF/NGF neurotrophic factor.

Without being bound to any particular theory of the invention, it is believed that the OP/BMP morphogens and GDNF/NGF neurotrophic factors exert a synergistic effect in promoting the survival and/or growth of neural tissues, and in inhibiting death or degeneration of neural tissues, by acting through separate receptor-based signaling pathways. In particular, it is believed that the OP/BMP proteins act through serine/threonine kinase receptors and that the GDNF/NGF neurotrophic factors of the invention act through tyrosine kinase receptors such that, when an OP/BMP morphogen and a GDNF/NGF neurotrophic factor are administered in combination, both the serine/threonine kinase and the tyrosine kinase signal transduction pathways are activated and a synergistic effect is produced.

Thus, the OP/BMP morphogens have been shown to act through serine/threonine kinase receptors, and these receptors have been shown to be expressed in both peripheral and central nervous system tissues. For example, it has been shown by in situ hybridization that several classes of peripheral neurons express BMP type II serine/threonine kinase receptors known to bind members of the OP/BMP morphogen family (Liu et al., *Mol. Cell. Biol.* 15:3479-3486 (1995); Rosenzweig et al., *Proc. Natl. Acad. Sci.* (*USA*) 92:7632-7636 (1995)), and that both OP/BMP type I and type II serine/threonine receptors are expressed in the CNS. Söderström et al., *Cell Tiss. Res.* 286:269-279 (1996a); Nosrat et al., *Cell Tiss. Res.* 286:191-207 (1996).

Similarly, the GDNF/NGF neurotrophic factors have been shown to act through specific tyrosine kinase receptors which are expressed in neural tissues. Thus, for example, the signaling pathway of GDNF has been shown to involve the activation of the tyrosine kinase receptor Ret (Trupp et al., *Nature* 381:785-789 (1996)), which is expressed in neural tissues including sympathetic, nodose and ciliary ganglia. Similarly, NT-3 acts via the TrkC receptor and, to some extent, via the TrkA receptor. See, e.g., Ebendal, *J. Neurosci. Res.* 32:461-470 (1992). These receptors are expressed in the brain and spinal cord as well as peripheral neurons. See, e.g., Vazquez and Ebendal, *Neuro Report* 2:593-596 (1991); Pei and Ebendal, *Exp. Neurol.* 132:105-115 (1995); Söderström et al., *Dev. Brain Res.* 85:96-108 (1995); Hallböök et al, *Int. J. Dev. Biol.* 39: 855-868 (1995); Williams and Ebendal, *Neuro Report* 6:2277-2282 (1995); Williams et al, *Eur. J. Neurosci.* 7:116-128 (1995).

Thus, in one aspect, the present invention provides methods of promoting the survival and/or growth of neural tissues, or of inhibiting death or degeneration of neural tissues, by administering to a mammal an OP/BMP morphogen and a GDNF/NGF neurotrophic factor in combination, thereby activating both the OP/BMP-activated serine/threonine kinase pathway and the GDNF/NT-activated tyrosine kinase pathway. In another aspect, the present invention provides for new pharmaceutical preparations for use in promoting the survival and/or growth of neural tissues, or of inhibiting death or degeneration of neural tissues, and comprising an OP/BMP morphogen and a GDNF/NGF neurotrophic factor in combination.

In another aspect, the present invention provides methods and pharmaceutical preparations for the treatment of non-neural tissues. In particular, there are a variety of non-neural tissues which express OP/BMP-activated serine/threonine kinase receptors and GDNF-activated tyrosine kinase receptors, including renal tissue and many thyroid papillary carcinomas (see, e.g., Schuchardt et al., *Nature* 367: 380-383 (1994); Pachnis et al., *Development* 119:1005-1017 (1993)). Therefore, the present invention also provides methods of promoting the survival and/or growth of such non-neural tissues, or of inhibiting death or degeneration of such non-neural tissues, by administering to a mammal an OP/BMP morphogen and a GDNF/NGF neurotrophic factor in combination, thereby activating both the OP/BMP-activated serine/threonine kinase pathway and the GDNF/NT-activated tyrosine kinase pathway. Similarly, the present invention provides for new pharmaceutical preparations for use in promoting the survival and/or growth of such non-neural tissues, or of inhibiting death or degeneration of such non-neural tissues, and comprising an OP/BMP morphogen and a GDNF/NGF neurotrophic factor in combination.

A. OP/BMP Morphogens

The OP/BMP morphogens of the present invention are naturally occurring proteins, or functional variants of naturally occurring proteins, in the osteogenic protein/bone morphogenetic protein (OP/BMP) family within the TGF-β superfamily of proteins. That is, these proteins form a distinct subgroup, referred to herein as the "OP/BMP morphogens," within the loose evolutionary grouping of sequence-related proteins known as the TGF-β superfamily. Members of this protein family comprise secreted polypeptides that share common structural features, and that are similarly processed from a pro-protein to yield a carboxy-terminal mature protein. Within the mature protein, all members share a conserved pattern of six or seven cysteine residues defining a 97-106 amino acid domain, and the active form of these proteins is either a disulfide-bonded homodimer of a single family member, or a heterodimer of two different members. See, e.g., Massague, *Annu. Rev. Cell Biol.* 6:597 (1990); Sampath et al., *J. Biol. Chem.* 265:13198 (1990). For example, in its mature, native form, natural-sourced human OP-1 is a glycosylated dimer typically having an apparent molecular weight of about 30-36 kDa as determined by SDS-PAGE. When reduced, the 30 kDa protein gives rise to two glycosylated peptide subunits having apparent molecular weights of about 16 kDa and 18 kDa. The unglycosylated protein has an apparent molecular weight of about 27 kDa. When reduced, the 27 kDa protein gives rise to two unglycosylated polypeptide chains, having molecular weights of about 14 kDa to 16 kDa.

Typically, the naturally occurring OP/BMP proteins are translated as a precursor, having an N-terminal signal peptide sequence, a "pro" domain, and a "mature" protein domain. The signal peptide is typically less than 30 residues, and is cleaved rapidly upon translation at a cleavage site that can be predicted using the method of Von Heijne, *Nucleic Acids Research* 14:4683-4691 (1986). The "pro" domain is variable both in sequence and in length, ranging from approximately 200 to over 400 residues. The pro domain is cleaved to yield the "mature" C-terminal domain of approximately 115-180 residues, which includes the conserved six- or seven-cysteine C-terminal domain of 97-106 residues. As used herein, the "pro form" of an OP/BMP family member includes a protein comprising a folded pair of polypeptides, each comprising a pro domain in either covalent or noncovalent association with the mature domains of the OP/BMP polypeptide. Typically, the pro form of the protein is more soluble than the mature form under physiological conditions. The pro form appears to be the primary form secreted from cultured mammalian cells. The "mature form" of the protein includes a mature C-terminal domain which is not associated, either covalently or noncovalently, with the pro domain. Any preparation of OP-1 is considered to contain mature form when the amount of pro domain in the preparation is no more than 5% of the amount of "mature" C-terminal domain.

OP/BMP family members useful herein include any of the known naturally-occurring native proteins including allelic, phylogenetic counterpart and other variants thereof, whether naturally-sourced or biosynthetically produced (e.g., including "muteins" or "mutant proteins"), as well as new, active members of the OP/BMP family of proteins.

Particularly useful sequences include those comprising the C-terminal seven cysteine domains of mammalian, preferably human, human OP-1, OP-2, OP-3, BMP2, BMP3, BMP4, BMP5, BMP6, BMP8 and BMP9. Other proteins useful in the practice of the invention include active forms of GDF-5, GDF-6, GDF-7, DPP, Vgl, Vgr-1, 60A, GDF-1, GDF-3, GDF-5, GDF-6, GDF-7, BMP10, BMP11, BMP13, BMP15, UNIVIN, NODAL, SCREW, ADMP or NURAL and amino acid sequence variants thereof. In one currently preferred embodiment, the OP/BMP morphogens of the invention are selected from any one of: OP-1, OP-2, OP-3, BMP2, BMP3, BMP4, BMP5, BMP6, and BMP9.

Publications disclosing these sequences, as well as their chemical and physical properties, include: OP-1 and OP-2: U.S. Pat. No. 5,011,691, U.S. Pat. No. 5,266,683, and Ozkaynak et al., *EMBO J.* 9:2085-2093 (1990); OP-3: WO94/10203; BMP2, BMP3, and BMP4: U.S. Pat. No. 5,013,649, WO91/18098, WO88/00205, and Wozney et al, *Science* 242:1528-1534 (1988); BMP5 and BMP6: WO90/11366 and Celeste et al, *Proc. Natl. Acad. Sci.* (USA) 87:9843-9847 (1991); Vgr-1: Lyons et al., *Proc. Natl. Acad. Sci.* (USA) 86:4554-4558 (1989); DPP: Padgett et al, *Nature* 325:81-84 (1987); Vgl: Weeks, *Cell* 51:861-867 (1987); BMP9: WO95/33830; BMP10: WO94/26893; BMP-11: WO94/26892; BMP12: WO95/16035; BMP-13: WO95/16035; GDF-1: WO92/00382 and Lee et al., *Proc. Natl. Acad. Sci.* (USA) 88:4250-4254 (1991); GDF-8: WO94/21681; GDF-9: WO94/15966; GDF-10: WO95/10539; GDF-11: WO96/01845; BMP-15: WO96/36710; MP121: WO96/01316; GDF-5 (CDMP-1, MP52): WO94/15949, WO96/14335, WO93/16099 and Storm et al., *Nature* 368:639-643 (1994); GDF-6 (CDMP-2, BMP13): WO95/01801, WO96/14335 and WO95/10635; GDF-7 (CDMP-3, BMP12): WO95/10802 and WO95/10635; BMP-3b: Takao et al., *Biochem. Biophys. Res. Comm.* 219:656-662 (1996); GDF-3: WO94/15965; 60A: Basler et al., *Cell* 73:687-702 (1993) and GenBank Accession No. L12032. In another embodiment, useful proteins include biologically active biosynthetic constructs, including novel biosynthetic proteins and chimeric proteins designed using sequences from two or more known OP/BMP family proteins. See also the biosynthetic constructs disclosed in U.S. Pat. No. 5,011,691, the disclosure of which is incorporated herein by reference (e.g., COP-1, COP-3, COP-4, COP-5, COP-7, and COP-16).

In other preferred embodiments, the OP/BMP morphogens useful herein include proteins which comprise an amino acid sequence sharing at least 70% amino acid sequence "homology" and, preferably, 75% or 80% homology with the C-terminal seven cysteine domain present in the active forms of human OP-1 (i.e., residues 330-431, as shown in SEQ ID NO: 2 of U.S. Pat. No. 5,266,683). In other preferred embodiments, the OP/BMP morphogens useful herein include proteins which comprise an amino acid sequence sharing at least 60% amino acid sequence identity and, preferably, 65% or 70% identity with the C-terminal seven cysteine domain present in the active forms of human OP-1. Thus, a candidate amino acid sequence can be aligned with the amino acid sequence of the C-terminal seven cysteine domain of human OP-1 using the method of Needleman et al., *J. Mol. Biol.* 48:443-453 (1970), implemented conveniently by computer programs such as the Align program (DNAstar, Inc.). As will be understood by those skilled in the art, homologous or functionally equivalent sequences include functionally equivalent arrangements of the cysteine residues within the conserved cysteine skeleton, including amino acid insertions or deletions which alter the linear arrangement of these cysteines, but do not materially impair their relationship in the folded structure of the dimeric protein, including their ability to form such intra- or inter-chain disulfide bonds as may be necessary for biological activity. Therefore, internal gaps and amino acid insertions in the candidate sequence are ignored for purposes of calculating the level of amino acid sequence homology or identity between the candidate and reference sequences.

"Amino acid sequence homology" is understood herein to include both amino acid sequence identity and similarity. Thus, as used herein, a percentage "homology" between two amino acid sequences indicates the percentage of amino acid residues which are identical or similar between the sequences. "Similar" residues are "conservative substitutions" which fulfill the criteria defined for an "accepted point mutation" in Dayhoff el al., *Atlas of Protein Sequence and Structure* Vol. 5 (Suppl. 3), pp. 354-352 (1978), Natl. Biomed. Res. Found., Washington, D.C. Thus, "conservative amino acid substitutions" are residues that are physically or functionally similar to the corresponding reference residues, having similar size, shape, electric charge, and/or chemical properties such as the ability to form covalent or hydrogen bonds, or the like. Examples of conservative substitutions include the substitution of one amino acid for another with similar characteristics, e.g., substitutions within the following groups: (a) valine, glycine; (b) glycine, alanine; (c) valine, isoleucine, leucine; (d) aspartic acid, glutamic acid; (e) asparagine, glutamine; (f) serine, threonine; (g) lysine, arginine, methionine; and (h) phenylalanine, tyrosine. The term "conservative substitution" or "conservative variation" also includes the use of a substituted amino acid in place of an unsubstituted parent amino acid in a given polypeptide chain, provided that the resulting substituted polypeptide chain has biological activity useful in the present invention.

The OP/BMP morphogens of the invention are characterized by biological activities which may be readily ascertained by those of ordinary skill in the art. Specifically, an OP/BMP morphogen of the present invention is capable of inducing osteogenesis in the Reddi-Sampath ectopic bone assay (Sampath and Reddi, *Proc. Natl. Acad. Sci.* (*USA*) 78:7599-7603 (1981)) or a substantially equivalent assay.

The Reddi-Sampath ectopic bone assay is well known in the art as an assay of osteogenic activity. The assay, which can be easily performed, is described and discussed in, for example, Sampath and Reddi, *Proc. Natl. Acad. Sci.* (*USA*) 78:7599-7603 (1981); and Wozney, "Bone Morphogenetic Proteins," *Progress in Growth Factor Research* 1:267-280 (1989). Many equivalent assays, using other animals and tissue sites, may be employed or developed by those of skill in the art to evaluate the biological activity of the OP/BMP morphogens of the present invention. See, for example, the bioassays described in U.S. Pat. No. 5,226,683.

The OP/BMP morphogens contemplated herein can be expressed from intact or truncated genomic or cDNA or from synthetic DNAs in prokaryotic or eukaryotic host cells. The dimeric proteins can be isolated from the culture media and/or refolded and dimerized in vitro to form biologically active preparations. Heterodimers can be formed in vitro by combining separate, distinct polypeptide chains. Alternatively, heterodimers can be formed in a single cell by co-expressing nucleic acids encoding separate, distinct polypeptide chains. See, for example, WO93/09229, or U.S. Pat. No. 5,411,941, for several exemplary recombinant heterodimer protein production protocols. Currently preferred host cells include, without limitation, prokaryotes including *E. coli*, or eukaryotes including yeast such as *Saccharomyces*, insect cells, or mammalian cells, such as CHO, COS or BSC cells. One of ordinary skill in the art will appreciate that other host cells can be used to advantage. Detailed descriptions of the proteins useful in the practice of this invention, including how to make, use and test them for osteogenic activity, are disclosed in numerous publications, including U.S. Pat. Nos. 5,266,683 and 5,011,691, the disclosures of which are herein incorporated by reference.

B. GDNF/NGF Neurotrophic Factors

The GDNF/NGF neurotrophic factors useful in the methods and preparations of the present invention include polypeptides, as well as functional variants of polypeptides, comprising at least the active portion of a mature mammalian protein selected from the group consisting of GDNF, BDNF, NGF, NT-3, NT-4, NT-5 and NT-6. Each of these preferred GDNF/NGF neurotrophic factors is discussed separately below.

1. GDNF. Glial cell-derived neurotrophic factor (GDNF) is a neurotrophic factor that belongs to the transforming growth factor-β (TGF-β) superfamily, but not to the OP/BMP family within the TGF-β superfamily. GDNF displays potent survival and differentiation-promoting effects for dopaminergic neurons both in vitro. Lin et al., *Science* 260:1130-1132 (1993)) and in vivo in animal models (Hudson et al., *Brain Res. Bull.* 36:425-432 (1995); Hoffer et al., *Neurosci. Lett.* 182:107-111 (1994). GDNF has also been shown to have neurotrophic effects for cholinergic motor neurons of the brain stem and spinal cord. Oppenheim et al, *Nature* 373:344-346 (1995); Yan et al., *Nature* 373:341-344 (1995). Descriptions of the active portion of a mature mammalian GDNF protein can be found in, for example, Lin et al., *Science* 260:1130-1132 (1993); Lin et al., *J. Neurochem.* 63: 758-768 (1994); and PCT Publication WO97/11965. In brief, GDNF is synthesized as a precursor and secreted as a mature protein comprising 134 amino acids, including the seven cysteine domain which characterizes the TGF-β superfamily of proteins. A 133 amino acid variant of GDNF in which the initial Met residue has been omitted ([Met$^{-1}$]GDNF) has substantially equivalent biological activity. See, e.g., WO97/11965. As used herein, the term "GDNF" includes a polypeptide comprising at least the 134 amino acid mature form, as well as a functional variant of the polypeptide, such as a conservative amino acid substitution variant or the 133 amino acid variant.

2. NGF. Nerve growth factor (NGF) is the best characterized member of the "neurotrophin" protein family, other members of which include brain-derived neurotrophic factor (BDNF), neurotrophin-3 (NT-3), neurotrophin-4 (NT-4), neurotrophin-5 (NT-5), and neurotrophin-6 (NT-6), discussed below. NGF has been shown to play a role in the regulation of the initial stages of dendritic growth, and to aid in promoting the survival, growth and/or repair of cholinergic neurons, and maintaining the differentiated phenotype of cholinergic neurons. For example, NGF can cause a subpopulation of nodose neurons to form dendrites in culture (De Koninck et al., *J. Neurosci.* 13:577-585 (1993)) and can enhance the growth of sympathetic dendrites when injected in situ (Snider, *J. Neurosci.* 8:2628-2634 (1988)). NGF alone, however, does not support dendritic growth in cultures of sympathetic neurons. Bruckenstein and Higgins, *Dev. Biol.* 128:324-336 (1988). In addition, NGF has been shown to be effective in preventing or even reversing the atrophy of cholinergic neurons induced in a standard fimbria/formix axotomy model of Alzheimer's Disease. See, e.g., Batchelor et al., *J. Comp. Neurol.* 284:187-204 (1989); Hefti et al., *J. Neurobiol.* 25:1418-1435 (1994); Olson et al., *Neurochem. J.* 25:1-3 (1994). As used herein, the term "NGF" includes a polypeptide comprising at least the mature form, as well as a functional variant of the polypeptide, such as a conservative amino acid substitution variant.

3. BDNF. Brain-derived neurotrophic factor (BDNF), another member of the neurotrophin family of proteins, has been shown to enhance dopamine uptake by fetal nigral DA neurons in cell culture (Beck et al., *Neurosci.* 52:855-866 (1993); Knusel et al., *Proc. Natl. Acad. Sci.* (*USA*) 88:961-969 (1991)) and to partially protect DA neurons from the toxic effects of the neurotoxins N-methyl-4-phenylpyridinium ion and 6-hydroxydopamine (6-ODHA). Hyman et al., *Nature* 350:230-232 (1991). BDNF has also been shown to have a strong supportive effect on the survival of cultured nigral DA neurons. Beck et al., *Neurosci.* 52:855-866 (1993); Hyman et al., *Nature* 350:230-232 (1991); Knusel et al., *Proc. Natl. Acad. Sci.* (*USA*) 88:961-965 (1991). These findings suggested that BDNF might have a survival-promoting effect on grafted DA neurons in vivo. BDNF treatment enhances the behavioral effect of grafted nigral DA neurons to the DA-depleted striatum of unilaterally 6-ODHA-lesioned rats as manifested by a relative reduction in amphetamine-induced turning at two weeks post-grafting. Sauer et al., *Brain Research* 626:37-44 (1993). However, this study failed to established any clear cut difference between treated and control animals in the extent of neurite outgrowth from the grafted DA neurons. Thus, although infusion with BDNF produced several behavioral and morphological effects in rats grafted with fetal nigral tissue, it was unable to increase the survival rates of the transplanted dopamine cells. As used herein, the term "BDNF" includes a polypeptide comprising at least the mature form, as well as a functional variant of the polypeptide, such as a conservative amino acid substitution variant.

4. NT-3. As used herein, "NT-3" means a human protein, or mammalian homologues thereof, having a protein sequence essentially as published at Jones et al., *Proc. Natl. Acad. Sci. (USA)* 87:8060-8064 (1990); Maisonpierre et al., *Genomics* 10:558-568 (1991); Kaisho et al., *FEBS Lett.* 266:187-191 (1990); WO 91/03569; and available through GenBank Accession No. M37763. The isolation and/or characterization of human NT-3 is described in, for example, Jones e al., *Proc. Natl. Acad. Sci. (USA)* 87:8060-806 (1990); and Maisonpierre et al., *Science* 247:1446-1451 (1990). The mouse NT-3 sequence is disclosed in Hohne et al., *Nature* 344:339-341 (1990); WO 91/03569, and GenBank Accession No. X53257. The rat NT-3 gene sequence is disclosed in Ernfors et al., *Proc. Natl. Acad. Sci. (USA)* 87:5454-5458 (1990); WO 91/03569; and GenBank Accession No. M34643. Comparison of the human NT-3 precursor to the rat and mouse NT-3 precursors reveals that the mature forms are identical. The gene for human NT-3 encodes a putative 257 amino acid precursor with an 18 amino acid signal peptide which is processed to a 119 amino acid mature peptide. NT-3 RNA has been detected in human CNS tissues including the cerebellum, nucleus basalis, basal ganglia, hippocampus and visual cortex. Maisonpierre et al., *Genomics* 10:558-568 (1991). Human NT-3 shares 56% amino acid identity with human NGF and human BDNF, and shares the conserved 6 cysteine with other members of the neurotrophin family, with the regions of greatest homology between the three proteins being clustered around these cysteine residues. The term "NT-3," as used herein, includes a polypeptide comprising at least the mature 119 amino acid form as disclosed in Jones et al., *Proc. Natl. Acad. Sci. (USA)* 87:8060-806 (1990), as well as a functional variant of the polypeptide, such as a conservative amino acid substitution variant.

5. NT-4. As used herein, "NT-4" means a human protein, or mammalian homologues thereof, having a protein sequence essentially as published at Ip et al., *Proc. Natl. Acad. Sci. (USA)* 89:3060-3064 (1992); U.S. Pat. No. 5,364,769; and available through GenBank Accession No. M86528. The isolation and/or characterization of NT-4 is described in, for example, Ip et al., *Proc. Natl. Acad. Sci. (USA)* 89:3060-3064 (1992); Hallböök et al., *Neuron* 6:845-858 (1991); and Ibanez et al., *Development* 117:1345-1353 (1993). The complete NT-4 gene sequence encodes a 236 amino acid, 27 kD precursor protein comprising a putative signal peptide sequence and pro-region of approximately 60 amino acids, which is believed to be processed to a 130 amino acid mature human NT-4 polypeptide. The mature form of NT-4 shares 46.5%, 55.4% and 52.2% sequence identity with NGF, BDNF, and NT-3, respectively. NT-4 contains the conserved 6 cysteines of the neurotrophin family, but contains a seven amino acid insertion located between the second and third cysteines. NT-4 has been demonstrated to support the survival of neurons of the trigeminal ganglion in the mouse (Ibanez et al., *Development* 117:1345-1353 (1993)) and dorsal root ganglia in the chicken (Ip et al., *Proc. Natl. Acad. Sci. (USA)* 89:3060-3064 (1992)). In the rat, NT-4 mRNA has been found in spinal cord and several brain regions including cerebellum and cortex. The term "NT-4," as used herein, includes a polypeptide comprising at least the mature 130 amino acid form as disclosed in Ip et al., *Proc. Natl. Acad. Sci. (USA)* 89:3060-3064 (1992), as well as a functional variant of the polypeptide, such as a conservative amino acid substitution variant.

6. NT-5. As used herein, the term "NT-5" means a human protein, or mammalian homologue thereof, having a protein sequence essentially as described in Berkemeier et al., *Neuron* 7:857-866 (1991). The isolation and/or characterization of NT-5 is described in, for example, Berkemeier et al., *Neuron* 7:857-866 (1991) and Berkemeier et al., *Som. Cell Mol. Genet.* 18:233-245 (1992). The human gene for NT-5 encodes a putative 210 amino acid, 22.4 kD precursor protein. The assigned initiation codon is followed by a putative signal sequence cleavage site at Ser-24. The putative pre-pro sequence of NT-5 is approximately 50 amino acids shorter than those of the other neurotrophins. The overall homology of the NT-5 precursor with *Xenopus* NT4, human NT-3, human BDNF and human NGF is 52%, 45%, 47% and 41%, respectively. The mature NT-5 is 123 amino acids long and shares the 6 cysteines conserved in the neurotrophin family. NT-5 shares 50% homology with NGF, 56% homology with BDNF, 55% homology with NT-3 and 66% homology with *Xenopus* NT-4. The rat NT-5 gene encodes a 209 amino acid protein that is 91% identical to its human counterpart. Berkemeier et al., *Neuron* 7:857-866 (1991). NT-5 protein has been identified in adult rat brain, and acts as a survival factor for dorsal root ganglion sensory cells and promotes survival and neurite outgrowth from sympathetic ganglion neurons. Berkemeier et al., *Neuron* 7:857-866 (1991). The term "NT-5," as used herein, includes a polypeptide comprising the mature 123 amino acid form, as well as a functional variant of the polypeptide, such as a conservative amino acid substitution variant.

7. NT-6. As used herein, "NT-6" means a human protein, or mammalian homologue thereof, having a protein sequence essentially as described in Gotz et al., *Nature* 327:266-269; WO 95/26363 (1994); and available through GenBank Accession Nos. L36325 and L36942. The isolation and characterization of NT-6 is described in, for example, Gotz et al., *Nature* 327:266-269 (1994). The NT-6 precursor contains 286 amino acids, having a hydrophobic domain at the N terminus (residues 1-19) characteristic of a signal peptide, and a putative pro-region at residues 20-142. The putative mature protein begins at residue 143. NT-6 shares the conserved 6 cysteines found in all neurotrophins, but contains a 22 residue insert between the second and third conserved cysteine containing domain. The term "NT-6," as used herein, includes a polypeptide comprising the mature 119 amino acid form disclosed in Gotz et al., *Nature* 327:266-269 (1994), as well as a functional variant of the polypeptide, such as a conservative amino acid substitution variant.

C. Subjects for Treatment

Subjects for treatment according to the methods of the present invention include, without limitation, (1) those having neural tissues which have been damaged, or are at imminent risk of damage, due to mechanical traumas such as arise from blunt force traumas to the head, cerebral edema, subdural haematoma, broken or crushed vertebra, or torn or severed nerves (including those arising from surgical procedures); (2) those which have suffered, or are at imminent risk of suffering, chemical traumas to nervous tissue as may arise, for example, from exposure to neurotoxins (e.g., lead, ethanol, ammonia, formaldehyde, mercury) or the administration of chemotherapeutic agents with neurotoxic side effects (e.g., cisplatin); (3) those which have suffered, or are at imminent risk of, an ischemic injury to neural tissues (e.g., cerebral stroke); and (4) those afflicted with, or at imminent risk of, a neuropathy or neurodegenerative disease. Particularly contemplated is the treatment of human subjects diagnosed with, or at imminent risk of, a neuropathy or neurodegenerative disease selected from the group consisting of amyotrophic lateral sclerosis (ALS), progressive muscular atrophy, hereditary motor and sensory neuropathy (Charcot-Marie-Tooth disease), Alzheimer's Disease, epilepsy, Huntington's Disease, Parkinson's Disease, palsy, dementia, Shy-Drager disease, Wernicke-Korsakoff syndrome, and Hallervorden-Spatz disease.

Diseases such as ALS, progressive muscular atrophy, and hereditary motor and sensory neuropathy (Charcot-Marie-Tooth disease) all result, at least in part, from degeneration of motor neurons which are located in the ventral horn of the spinal cord. Thus, in one embodiment, the present invention provides for methods and preparations which employ an OP/BMP morphogen in combination with a GDNF/NGF neurotrophic factor for the treatment of these and other conditions involving loss of or damage to motor neurons.

The hippocampus, a well-defined structure that is part of the cerebral cortex of the brain, is important in the formation of long term memory. Degeneration of pyramidal CA1 neurons, which are located in the CA1 region of the hippocampus, is one characteristic of Alzheimer's disease. These same neurons are selectively vulnerable to ischemic and anoxic damage which occurs in conditions such as stroke and head trauma. In addition, the CA1 pyramidal hippocampal neurons as well as pyramidal neurons located in the CA3 region of the hippocampus are selectively injured in epilepsy. Thus, in one embodiment, the present invention provides for methods and preparations which employ an OP/BMP morphogen in combination with a GDNF/NGF neurotrophic factor for the treatment of these and other conditions involving loss of or damage to hippocampal neurons.

The majority of neurons in the striatum utilize GABA (4-aminobutyric acid) as their neurotransmitter, and may be referred to as "GABAnergic" neurons. The striatum is also the major target of the progressive neurodegeneration that occurs in Huntington's disease, in which striatal GABA-utilizing neurons (e.g., spiny cell neurons and enkephalin neurons) atrophy and/or die. Thus, in one embodiment, the present invention provides for methods and preparations which employ an OP/BMP morphogen in combination with a GDNF/NGF neurotrophic factor for the treatment of this and other conditions involving loss of or damage to striatal or GABAnergic neurons.

Dopamine-producing ("dopaminergic" or "DA") neurons are located primarily in the substantia nigra and, to a lesser extent, in the adjacent striatum (comprising the caudate nucleus, putamen, pallidum and locus coerulus). The neurons of the striatum express receptors for dopamine and are responsible for control of motor activity. Thus, degeneration of DA neurons results in a decrease of dopamine levels and loss of motor activity. In particular, the progressive degeneration of dopaminergic neurons in the substantia nigra can lead to the slowing of initiation and execution of voluntary muscle movement (bradykinesis), the muscular rigidity, and tremor which are characteristic of Parkinson's Disease. Thus, in one embodiment, the present invention provides for methods and preparations which employ an OP/BMP morphogen in combination with a GDNF/NGF neurotrophic factor for the treatment of this and other conditions involving loss of or damage to dopaminergic neurons, including those of the substantia nigra.

Other neuropathic conditions in which populations of neural cells are lost or damaged include palsy, dementia, Shy-Drager disease, Wernicke-Korsakoff syndrome, and Hallervorden-Spatz disease. Thus, in other embodiments, the present invention provides for methods and preparations which employ an OP/BMP morphogen in combination with a GDNF/NGF neurotrophic factor for the treatment of these and other conditions involving loss of or damage to neural tissues.

D. Pharmaceutical Preparations

The pharmaceutical preparations of the present invention include at least one OP/BMP morphogen in combination with at least one GDNF/NGF neurotrophic factor. Preferably, such preparations include an amount of each agent which is effective when administered by alone. Because of the synergistic effect of the agents in combination, however, the pharmaceutical preparations may contain an amount of each agent which, when administered in the absence of the other, would not be effective alone. The determinations of appropriate ratios of the agents is within the ability and discretion of one of ordinary skill in the art for the treatment of a given condition, for a given combination of OP/BMP morphogen and GDNF/NGF neurotrophic factor, and given route of administration.

As a general matter, the pharmaceutical preparations of the present invention, including at least one OP/BMP morphogen and at least one GDNF/NGF neurotrophic factor can be tested using in vitro assays, animal models, and clinical studies. Effective concentrations of the preparations are those sufficient to (1) cause enhanced neurite outgrowth in an in vitro assay of neuronal growth; (2) cause motor skill improvements in a standard animal model of Parkinson's disease; or (3) cause a clinically significant improvement in neurological function when administered to a mammalian subject (e.g., a human patient).

E. Methods and Formulations for Administration

The pharmaceutical preparations of the present invention, including at least one OP/BMP morphogen and at least one GDNF/NGF neurotrophic factor, can be administered to an individual by any suitable means, preferably directly (e.g., locally, as by injection to a tissue locus) or systemically (e.g., parenterally or orally). Where the preparation is to be administered parenterally, such as by intravenous, subcutaneous, intramuscular, intraorbital, ophthalmic, intraventricular, intracranial, intracapsular, intraspinal, intracisternal, intraperitoneal, or buccal administration, the preparation preferably comprises part of an aqueous solution. The solution is chosen to be physiologically acceptable such that, in addition to delivery of the desired OP/BMP morphogen and GDNF/NGF neurotrophic factor to the patient, the solution does not otherwise adversely affect the patient's electrolyte and volume balance.

Useful solutions for parenteral administration can be prepared by a variety of methods well known in the pharmaceutical arts. See, e.g., *Remington's Pharmaceutical Sciences*. Gennaro, A., ed., Mack Pub., (1990). Formulations can include, for example, polyalkylene glycols such as polyethylene glycol, oils of vegetable origin, hydrogenated naphthalenes, and the like. Formulations for direct administration, in particular, can include glycerol and other preparations of high viscosity. Biocompatible, preferably bioresorbable, polymers, including, for example, hyaluronic acid, collagen, polybutyrate, tricalcium phosphate, lactide and lactide/glycolide copolymers, can be useful excipients to control the release of the preparation in vivo. Other potentially useful parenteral delivery systems for these preparations include ethylene-vinyl acetate copolymer particles, osmotic pumps, implantable infusion systems, and liposomes.

As will be appreciated by those skilled in the art, the amounts and/or concentrations of the agents present in a pharmaceutical preparation will vary depending upon a number of factors, including the dosage of the drug to be administered, the chemical characteristics (e.g., hydrophobicity) of the agents employed, and the route of administration. The preferred dosage may also depend on such variables as the type and extent of the damage or injury to be treated, the overall health status of the subject, the relative biological efficacy of the agents employed, the presence of excipients or diluents, and the like.

As a general matter, the pharmaceutical preparations of the present invention are administered in amounts sufficient to achieve effective concentrations of the OP/BMP morphogen and the GDNF neurotrophic factor at a site of neural tissue damage or injury, or at a site of imminent risk of such injury. Preferably, the preparations contain an amount of an OP/BMP morphogen such that, when administered by the chosen route of administration, results in a concentration of the OP/BMP morphogen of about 0.1 ng/ml to 10 µg/ml, more preferably about 1 ng/ml to 100 ng/ml. Similarly, the preparations preferably contain an amount of a GDNF/NGF neurotrophic factor such that, when administered by the chosen route of administration, results in a concentration of the GDNF/NGF neurotrophic factor of about 0.1 ng/ml to 10 µg/ml, more preferably about 1 ng/ml to 100 ng/ml. Because of the synergistic interactions of the OP/BMP morphogens and GDNF/NGF neurotrophic factors, optimal concentrations and ratios will vary depending upon the particular agents employed.

Where injury to neurons of a neural pathway is induced deliberately as part of, for example, a surgical procedure, the OP/BMP morphogen and GDNF/NGF neurotrophic factor preferably are provided just prior to, or concomitant with induction of the trauma. Preferably, the morphogen and neurotrophic factor are administered prophylactically in a surgical setting.

Where the OP/BMP morphogen and neurotrophic factor are to be provided to a site to stimulate axon regeneration, the pharmaceutical preparation preferably is provided to the site in association with a biocompatible, preferably bioresorbable carrier suitable for maintaining the proteins at the site in vivo, and through which a neural process can regenerate. A currently preferred carrier also comprises sufficient structure to assist direction of axonal growth. Currently preferred carriers include structural molecules such as collagen, hyaluronic acid or laminin, and/or synthetic polymers or copolymers of, for example, polylactic acid, polyglycolic acid or polybutyric acid. Currently most preferred are carriers comprising tissue extracellular matrix. These can be obtained commercially. In addition, a brain tissue-derived extracellular matrix can be prepared as described in PCT Publication WO92/15323, incorporated herein by reference, and/or by other means known in the art.

The currently preferred means for repairing breaks in neural pathways, particularly pathways of the peripheral nervous system, include providing the OP/BMP morphogen and GDNF/NGF neurotrophic factor to the site as part of a device that includes a biocompatible membrane or casing of a dimension sufficient to span the break and having openings adapted to receive severed nerve ends. The OP/BMP morphogen and GDNF/NGF neurotrophic factor are disposed within the casing, preferably dispersed throughout a suitable carrier, and are accessible to the severed nerve ends. Alternatively, the OP/BMP morphogen and GDNF/NGF neurotrophic factor can be adsorbed onto the interior surface of the casing, or otherwise associated therewith. The casing acts as a nerve guidance channel, aiding in directing axonal growth. Suitable channel or casing materials include silicone or bioresorbable materials such as collagen, hyaluronic acid, laminin, polylactic acid, polyglycolic acid, polybutyric acid and the like.

EXAMPLES

OP/BMP Morphogen and GDNF/NGF Neurotrophic Factor Synergy

The OP/BMP morphogen and GDNF/NGF neurotrophic factor compositions described herein enhance process formation in neural cells. A variety of peripheral ganglia derived from embryonic chickens were used as a model for the induction of nerve fiber outgrowth by OP-1 (Creative Biomolecules, Hopkinton, Mass.) in combination with GDNF (PeproTech, Rocky Hill, N.J.), NT-3 (Austral Biologicals, San Ramon, Calif.), activin A (Austral Biologicals, San Ramon, Calif.), or mouse β-NGF.

Peripheral ganglia were obtained from embryonic day 9 (E9) chickens according to the method of Ebendal et al. (Ebendal, in *IBRO Handbook series: Methods in the Neurosciences* Vol. 12, pp. 81-93 (1989), John Wiley, Chichester). Sympathetic ganglia were obtained from the lumbar region. Ciliary ganglia were obtained from the orbit. Remak ganglia were obtained from the dorsal mesorectum. Dorsal root ganglia were obtained from the lumbo-sacral region. Nodose ganglia were obtained from the vagus nerve cranial to the heart. For some experiments, trigeminal ganglia were obtained and the maxillomandibular and ophthalmic lobes were separated before explantation. The ganglia were removed intact and maintained at 37° C. with 5% $CO_2$ in a collagen matrix or were dissociated into single neurons and spread into a thin collagen gel (Ebendal (1989), supra). In both instances, the gels were supplemented with equal volumes of Eagle's Basal Medium with 1% fetal calf serum. Control cultures consisted of Eagle's Basal Medium with 1% fetal calf serum, in some instances supplemented with the buffer (25 mM arginine, 150 mM NaCl, pH 9.0, 0.1% Tween 80) at concentrations to match the experimental culture dilutions. Cultures were treated with control medium, OP-1, NT-3, GDNF or NGF alone, or in various combinations and at a series of concentrations for 2, 4 and 6 days.

The 6 day cultures were fed with fresh medium containing the growth factors at day 4 post incubation. Whole ganglia were examined under dark-field illumination whereas dissociated neurons were examined using phase-contrast optics. Surviving cells were counted in a strip across the plate to calculate the survival relative to the survival of cells treated with NGF at 5 ng/ml for 2 days.

Previous studies have shown that NT-3 evokes fiber outgrowth in explanted ciliary ganglia and also elicits a weak response in sympathetic ganglia of the chicken embryo. Ernfors et al., *Proc. Natl. Acad. Sci.* (*USA*) 87:5454-5458 (1990). OP-1 greatly enhanced fiber outgrowth induced by NT-3 treatment in E9 sympathetic ganglia. The effects were apparent after 2 days in culture and persisted after 4 days of culture. Optimal concentrations of NT-3 and OP-1 were 10 ng/ml and 50 ng/ml, respectively. Treatment of ganglia cultures with OP-1 in combination with GDNF gave similar results. OP-1 did not stimulate fiber outgrowth of any of the whole explanted E9 ganglia at doses of 0.1 ng/ml to 1000 ng/ml. Further, OP-1 also failed to stimulate younger ganglia (e.g., from embryonic day 4.5). The buffer (pH 9) failed to exert any potentiating effect on the NT-3 responses in sympathetic, ciliary or nodose ganglia.

Treatment of ciliary ganglia with 10 ng/ml NT-3 and 50 ng/ml OP-1 resulted in robust fiber halos consisting of thick fascicles of neurites which radiated from the cell. Treatment of ciliary ganglia with 50 ng/ml GDNF and 50 ng/ml OP-1 gave a fiber halo of ciliary nerve fascicles after 2 days of culture. Ciliary ganglia extended fewer or less robust nerve fibers in response to NT-3 (2 ng/ml and 10 ng/ml) and GDNF (50 ng/ml) but did not extend neurites in response to 50 ng/ml OP-1 alone.

Figure 1B:
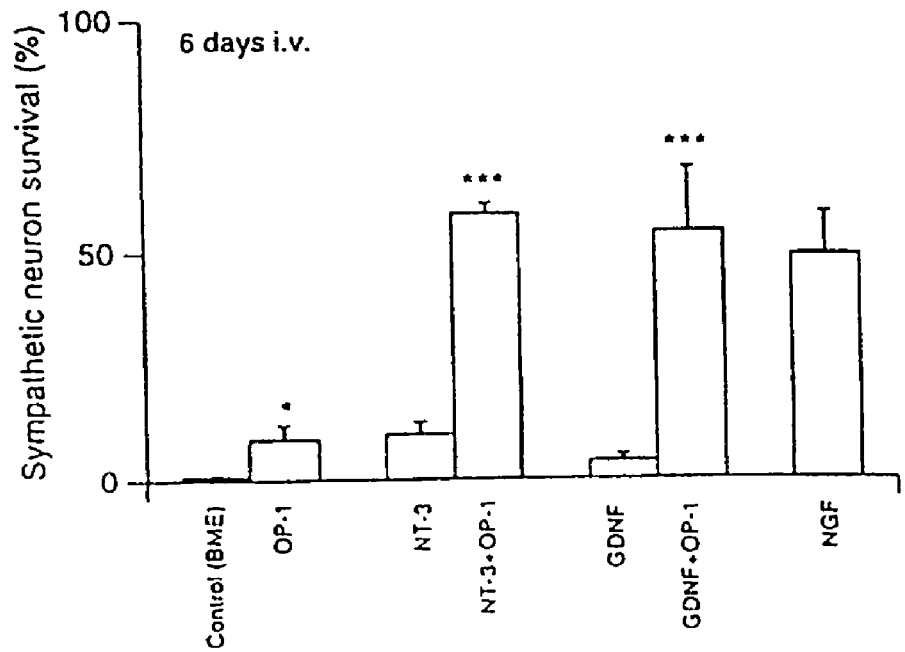

Thus treatment of neurons with a combination of OP-1 and NT-3, or OP-1 and GDNF, suggested a synergistic effect of OP-1 on NT-3 or GDNF induced neurite outgrowth. A statistical analysis also shows differences in survival to be significant (FIG. 1) as compared with the control (BME, or Basal Medium, Eagle's). Both OP-1 and NT-3 are required from the beginning of the treatment period to elicit the enhanced nerve outgrowth response in the ciliary ganglia.

Sensory neurons of the nodose ganglia were also treated with OP-1 (50 ng/ml) alone and in combination with NT-3 (2 ng/ml and 10 ng/ml) or OP-1 (50 ng/ml) in combination with GDNF (50 ng/ml). Treatment of sensory neurons with OP-1 alone did not elicit fiber outgrowth. However, OP-1 enhanced NT-3-induced neurite outgrowth after 2 and 4 days of treatment.

Activin A (20 ng/ml) did not mimic the effects of OP-1 when tested alone or in combination with NT-3 (10 ng/ml), GDNF (50 ng/ml) or NGF (5 ng/ml) in the treatment of sympathetic ganglia.

OP-1 is therefore capable of promoting NT-3 and GDNF induced nerve process formation in several classes of peripheral neurons.

Treatments for Alzheimer's Disease

Alzheimer's disease is a neurodegenerative disease in which there is significant neuronal loss of the large pyramidal cells of the parietal and frontal association areas, hippocampus and amagdyla. Cholinergic neurons of the basal forebrain and noradrenergic neurons of the locus coerulus are also severely affected.

In accordance with the present invention, an OP/BMP morphogen, preferably human OP-1, is administered to an Alzheimer's patient in combination with a GDNF/NGF neurotrophic factor, preferably GDNF or NT-3, in order to promote the growth and survival of cells in this region, as well as to inhibit the progressive loss of additional neuronal cells.

An aqueous, pharmaceutical preparation comprising an OP/BMP morphogen and GDNF/NGF neurotrophic factor is administered to the patient parenterally. Preferably, the preparation is administered intracerebrally by, for example, intracerebroventricular or intrathecal injection or infusion. In one embodiment, the cranium of the subject is immobilized in a stereotaxic device, a small hole is made in the skull, and the preparation is injected or infused directly into the affected regions of the brain. Dosages may be calculated to achieve concentrations of the OP/BMP morphogen and GDNF/NGF neurotrophic factor of about 0.1-10 µg/ml, preferably about 1-100 ng/ml at the site of injection. Alternatively, dosages may be calculated to deliver about 10-100 µg/kg of the morphogen and neurotrophic factor, preferably 1-25 µg/kg. Dosages are repeated daily or less frequently for a period of several weeks to months or, if needed, on a regular basis throughout the life of the subject. Alternatively, a sustained release device is implanted within the brain of the subject to cause a continuous release of the preparation over an extended period.

Treatments for Severed Nerve Fibers

Due to the limited ability of mammalian nerve cells grow or regenerate, severed nerve fibers frequently lead to permanent loss of the sensory or motor function associated with the nerve. Nerve fibers may be torn or severed in accidents (e.g., vehicular accidents) or as an unavoidable side effect of surgery.

In accordance with the present invention, an OP/BMP morphogen, preferably human OP-1, is administered in combination with a GDNF/NGF neurotrophic factor, preferably GDNF or NT-3, to a subject having severed nerve fibers in order to promote reparative growth and survival of the damaged cells.

An aqueous, pharmaceutical preparation comprising an OP/BMP morphogen and GDNF/NGF neurotrophic factor is administered to the patient parenterally. In the case of damaged peripheral nerve fibers (e.g., in the sciatic nerve), the preparation is preferably administered in conjunction with the use of nerve guide channels which enclose the ends of the severed fibers and guide their growth together. In the case of severed fibers in the spinal cord, the preparation is preferably injected or infused into the CSF in the region of the injury. Dosages may be calculated to achieve concentrations of the OP/BMP morphogen and GDNF/NGF neurotrophic factor of about 0.1-10 µg/ml, preferably about 1-100 ng/ml at the site of injection or infusion. Alternatively, dosages may be calculated to deliver about 10-100 µg/kg of the morphogen and neurotrophic factor, preferably 1-25 µg/kg. In the case of a spinal injury, dosages are repeated daily or less frequently for a period of several weeks to months. Alternatively, in the case of severed peripheral nerves enclosed in nerve guidance channels, a sustained release formulation is employed in which the preparation is admixed with a matrix material within the nerve guidance channel.

Treatments for Stroke

Ischemic events, or strokes, in the brain may cause neural lesions which result in permanent loss of cognitive, sensory, or motor function. Immediately after the onset of a stroke, inhibition of the death or degeneration of cells in the ischemic area, as well as the promotion of growth and survival of these cells, is important to minimizing permanent damage.

In accordance with the present invention, an OP/BMP morphogen, preferably human OP-1, is administered in combination with a GDNF/NGF neurotrophic factor, preferably GDNF or NT-3, to a subject suffering from a stroke.

An aqueous, pharmaceutical preparation comprising an OP/BMP morphogen and GDNF/NGF neurotrophic factor is administered to the patient parenterally. Preferably, the preparation is administered intracerebrally by, for example, intracerebroventricular or intrathecal injection or infusion. Dosages may be calculated to achieve concentrations of the OP/BMP morphogen and GDNF/NGF neurotrophic factor of about 0.1-10 µg/ml, preferably about 1-100 ng/ml at the site of injection. Alternatively, dosages may be calculated to deliver about 10-100 µg/kg of the morphogen and neurotrophic factor, preferably 1-25 µg/kg. Dosages may be continuous or frequent for a period of several days to weeks. First dosages are preferably administered within the first few hours on the onset of the stroke.

What is claimed is:

1. A method for promoting the survival or growth of mammalian peripheral nervous system neural cells in vivo, wherein said neural cells express an OP/BMP-activated serine/threonine kinase receptor and a GDNF-activated tyrosine kinase receptor, comprising contacting said cells with an effective concentration of a preparation comprising (a) a GDNF neurotrophic factor, and (b) an OP/BMP morphogen comprising an amino acid sequence having at least 70% homology or 60% identity with the C-terminal seven cysteine skeleton of human OP-1, wherein said OP/BMP morphogen can induce ectopic bone;

wherein said OP/BMP morphogen and said GDNF neurotrophic factor act synergistically to promote survival of mammalian peripheral nervous system neural cells.

2. The method of claim 1, wherein said OP/BMP morphogen comprises an amino acid sequence having at least 80% homology with the C-terminal seven-cysteine skeleton of human OP-1.

3. The method of claim 1, wherein said OP/BMP morphogen comprises an amino acid sequence having at least 90% homology with the C-terminal seven-cysteine skeleton of human OP-1.

4. The method of claim 1, wherein said OP/BMP morphogen comprises an amino acid sequence having at least 70% identity with the C-terminal seven-cysteine skeleton of human OP-1.

5. The method of claim 1, wherein said OP/BMP morphogen is selected from the group consisting of OP-1, OP-2, OP-3, BMP2, BMP3, BMP4, BMP5, BMP6, and BMP9.

6. The method as of claim 1, wherein said GDNF neurotrophic factor is human GDNF.

7. The method of claim 1, wherein said preparation comprises between 1 ng/ml and 100 ng/ml of said OP/BMP morphogen.

8. The method of claim 1, wherein said preparation comprises between 1 ng/ml and 100 ng/ml of said GDNF neurotrophic factor.

9. The method of claim 1 wherein said preparation comprises between 1 ng/ml and 100 ng/ml of said OP/BMP morphogen and between 1 ng/ml and 100 ng/ml of said GDNF neurotrophic factor.

10. The method of claim 1, wherein said OP/BMP morphogen is op-1.

* * * * *